United States Patent
Colborn et al.

(10) Patent No.: US 6,670,487 B1
(45) Date of Patent: Dec. 30, 2003

(54) METHOD FOR REMOVING IMPURITIES FROM OXIDATION PRODUCTS

(75) Inventors: Robert Edgar Colborn, Niskayuna, NY (US); Farid Fouad Khouri, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/354,402

(22) Filed: Jan. 30, 2003

Related U.S. Application Data

(62) Division of application No. 10/174,096, filed on Jun. 18, 2002, now abandoned.

(51) Int. Cl.⁷ .................... C07D 307/89; C07D 307/92; C07D 311/78
(52) U.S. Cl. ................. 549/246; 549/232; 549/236; 549/248; 549/250; 562/416
(58) Field of Search ................ 549/232, 246, 549/250, 236, 248; 562/416

(56) References Cited

U.S. PATENT DOCUMENTS

| | | | |
|---|---|---|---|
| 2,925,425 A | * 2/1960 | Contois, Jr. et al. | ........ 562/409 |
| 4,165,324 A | 8/1979 | Schroeder et al. | |
| 4,436,922 A | 3/1984 | Kita et al. | |
| 5,229,482 A | 7/1993 | Brunelle | |
| 5,449,820 A | 9/1995 | Fukui et al. | |
| 5,770,764 A | 6/1998 | Zeitlin et al. | |
| 5,830,974 A | 11/1998 | Schmidhauser et al. | |
| 6,465,685 B1 | * 10/2002 | Phelps et al. | ................ 562/422 |

* cited by examiner

*Primary Examiner*—Bernard Dentz
(74) *Attorney, Agent, or Firm*—Andrew J. Caruso; Patrick K. Patnode

(57) ABSTRACT

Disclosed is a method for removing impurities from products derived from oxidation of an ortho-dialkylaromatic compound which comprises at least one step selected from the group consisting of extraction of an aqueous solution comprising aromatic dicarboxylic acid product with an organic solvent and extraction of an organic solution comprising aromatic anhydride product with an aqueous bicarbonate solution for a time period insufficient to allow hydrolysis of anhydride to acid.

53 Claims, No Drawings

METHOD FOR REMOVING IMPURITIES FROM OXIDATION PRODUCTS

CROSS-REFERENCE TO RELATED APPLICATIONS

This application is a division of application Ser. No. 10/174,096, filed Jun. 18, 2002 now abandoned, which is hereby incorporated by reference in its entirety.

BACKGROUND OF THE INVENTION

The present invention is related to a method for removing impurities from products derived from oxidation of ortho-dialkylaromatic compounds. In one embodiment the present invention is related to a method for removing impurities from products derived from oxidation of ortho-dimethylbenzenes. In another particular embodiment the present invention is related to a method for removing impurities from products derived from oxidation of halogenated ortho-dialkylbenzenes, and particularly from oxidation of halogenated ortho-dimethylbenzenes.

Aromatic ortho-dicarboxylic acids and their corresponding anhydrides are often produced by oxidation of ortho-dialkylaromatic compounds. A particular example is the well-known process for producing phthalic acid and phthalic anhydride by oxidation of ortho-xylene in the presence of a catalyst and oxygen source. Efficient processes for the production of halophthalic acid and halophthalic anhydride, such as chlorophthalic acid and chlorophthalic anhydride, via liquid-phase oxidation of halo-o-xylene using catalysts and an oxygen source have been recently described, for example in copending, commonly owned application Ser. No. 09/718,124, filed Nov. 20, 2000. In the preparation of chlorophthalic acid and chlorophthalic anhydride via liquid-phase oxidation, high first-pass yields are very important because intermediate products are difficult and expensive to separate from the product. When a mixture of 3-chloro-o-xylene and 4-chloro-o-xylene serves as starting material for the oxidation, the major impurities may comprise any of four chlorophthalides, or four chloro-toluic acids which may result from incomplete oxidation of the substrate. In the case of over oxidation one may obtain isomers of chlorobenzoic acid from decarboxylation or phthalic acid from dechlorination of the product, chlorophthalic acid. A problem is that neither conventional distillation nor recrystallization allows for a clean separation of the anhydrides from the phthalide or carboxylic acid impurities.

Elimination of impurities from oxidation product mixtures of ortho-dialkylaromatic compounds has in the past often relied on improving the oxidation process conditions to prevent impurity formation U.S. Pat. No. 4,436,922 teaches a process for conversion of impurities to desired products in a reoxidation process. Post-oxidation removal of impurities has been described in U.S. Pat. No. 4,165,324 wherein residual phthalide impurity is removed by treatment of an oxidation reaction mixture with alkali metal salts at high temperature. These approaches are deficient in that there is loss in yield, increase in color and increase in cost associated with the energy required to effect the reaction.

Extractions of liquid phase oxidation reaction mixtures have been described as a way to remove the metal catalyst components. Such extractions are usually done while the product is primarily insoluble in the aqueous phase as taught in U.S. Pat. No. 5,449,820. U.S. Pat. No. 5,770,764 utilizes aqueous solubility by employing trialkylamines to make the corresponding salts of oxidation products, followed by purifying the salts and recovering the acids.

Accordingly, there remains a need for an inexpensive and efficient method for removing organic impurities from products derived from oxidation of ortho-dialkylaromatic compounds. In particular, there is a need for a method for removing organic impurities from oxidation products comprising halophthalic acids and/or halophthalic anhydrides.

SUMMARY OF THE INVENTION

The present inventors have discovered a method for removing impurities from products derived from oxidation of an ortho-dialkylaromatic compound which comprises at least one step selected from the group consisting of extraction of an aqueous solution comprising aromatic dicarboxylic acid product with an organic solvent and extraction of an organic solution comprising aromatic anhydride product with an aqueous bicarbonate solution for a time period insufficient to allow hydrolysis of anhydride to acid.

Various other features, aspects, and advantages of the present invention will become more apparent with reference to the following description and appended claims.

DETAILED DESCRIPTION

In various embodiments products derived from oxidation of ortho-dialkylaromatic compounds comprise those derived from oxidation of substituted or unsubstituted xylene, or substituted or unsubstituted dimethylnaphthalene. Typical substituents, when present, on xylene or dimethylnaphthalene comprise alkyl or halo substituents. In some embodiments said products are those derived from oxidation of monohalo-ortho-xylene, in one particular embodiment from oxidation of 4-halo-ortho-xylene, and in other particular embodiments from oxidation of 4-fluoro- or 4-chloro-ortho-xylene. In another embodiment products are derived from oxidation of a mixture comprising 4-halo- and 3-halo-ortho-xylene, in some particular embodiments a mixture of 4-fluoro- and 3-fluoro-ortho-xylene and in other particular embodiments a mixture of 4-chloro- and 3-chloro-ortho-xylene. When 3-halo-ortho-xylene is present in a substrate for oxidation, it comprises in some embodiments about 0.001–35 molar percent, in other embodiments about 0.001–15 molar percent, in other embodiments about 0.01–12 molar percent, and in still other embodiments about 0.1–10 molar percent of total substrate.

In yet another embodiment products derived from oxidation of ortho-dialkylaromatic compounds comprise those derived from oxidation of at least one halo-ortho-xylene as described above, optionally in the presence of at least one halotoluic acid, in one embodiment at least one chlorotoluic acid (also known as chloro methylbenzoic acid), in another embodiment either (a) 4-chloro-2-methyl benzoic acid or (b) 5-chloro-2-methylbenzoic acid or (c) a mixture thereof, and in still another embodiment a mixture of either or both of (a) and (b) with either (d) 4-halo-ortho-xylene, or (e) a mixture of 4-halo- and 3-halo-ortho-xylene.

In still another embodiment products derived from oxidation of ortho-dialkylaromatic compounds comprise those derived from oxidation of a mixture of ortho-xylene with halo-ortho-xylene, in one embodiment either with (d) 4-halo-ortho-xylene, or with (e) a mixture of 4-halo- and 3-halo-ortho-xylene, or with at least one halotoluic acid, such as chlorotoluic acid, or with a mixture of halotoluic acid with either (d) 4-halo-ortho-xylene, or (e) a mixture of 4-halo- and 3-halo-ortho-xylene. When ortho-xylene is present in a substrate for oxidation, it typically comprises in one embodiment about 0.001–100 molar percent, in another embodiment about 0.001–10 molar percent and in still another embodiment about 0.01–1 molar percent of total substrate. In a particular embodiment products derived from oxidation of ortho-dialkylaromatic compounds comprise those derived from oxidation of 4-chloro-ortho-xylene, optionally in combination with at least one of 3-chloro-ortho-xylene, ortho-xylene, or chlorotoluic acid.

In various embodiments ortho-dialkylaromatic oxidation products comprise those obtained by oxidation of at least one of and sometimes both the two aromatic ortho-alkyl groups. In some embodiments ortho-dialkylaromatic oxidation products comprise those obtained by oxidation of at least one of and sometimes both of two aromatic ortho-methyl groups. In various embodiments the oxidation products comprise at least one of a substituted or unsubstituted aromatic ortho-dicarboxylic acid, or a substituted or unsubstituted aromatic anhydride derived from the corresponding aromatic ortho-dicarboxylic acid. In some particular embodiments the oxidation products comprise at least one of phthalic acid, phthalic anhydride, halotoluic acid, halophthalic acid, halophthalic anhydride, or mixtures thereof. In still other particular embodiments the oxidation products comprise at least one of phthalic acid, phthalic anhydride, chlorotoluic acid, 3-chlorophthalic acid, 3-chlorophthalic anhydride, 4chlorophthalic acid, 4-chlorophthalic anhydride, or mixtures thereof. In other particular embodiments the oxidation products comprise at least one of chlorotoluic acid, chlorophthalic acid, or chlorophthalic anhydride. It is to be understood that product mixtures initially comprising halophthalic acid may be dehydrated to form a product mixture comprising in some embodiments up to 100 mole % (based on halophthalic acid) of halophthalic anhydride. It is also to be understood that product mixtures initially comprising halophthalic anhydride may be hydrated to form a product mixture comprising in some embodiments up to 100 mole % (based on halophthalic anhydride) of halophthalic acid. In a particular embodiment the products comprise chlorotoluic acid and 4-chlorophthalic acid, optionally with 4-chlorophthalic anhydride. In another particular embodiment the products comprise chlorotoluic acids and a mixture of 3-chloro- and 4-chlorophthalic acid optionally with 3-chloro- and 4-chlorophthalic anhydride. When ortho-xylene is present in the oxidation substrate, then phthalic acid, optionally with phthalic anhydride and/or toluic acid may be present in the oxidation products.

The products derived from oxidation of ortho-dialkylaromatic compounds may comprise at least one solvent, which in some embodiments comprises a lower aliphatic carboxylic acid. Illustrative examples of lower aliphatic carboxylic acids, include, but are not limited to, acetic acid, propionic acid, butanoic acid, pentanoic acid, or hexanoic acid. Acetic acid is present in some embodiments. In some embodiments the said products are stripped to dryness to remove essentially all volatile materials, including, but not limited to, solvent before treatment by a method disclosed in various embodiments of the present invention.

In various embodiments the products derived from oxidation of ortho-dialkylaromatic compounds may further comprise at least one metal catalyst. The at least one metal catalyst typically comprises a metal compound with a metal selected from the group consisting of cobalt, manganese, vanadium, copper, molybdenum, and iron, and mixtures thereof. In some embodiments, a metal compound is a salt of the metal and in particular embodiments an acetate or acetylacetonate of the metal. Illustrative metal compounds include, but are not limited to, cobalt dibromide hexahydrate, cobalt dichloride, cobalt (II) acetate, cobalt (II) acetylacetonate, cobalt (III) acetylacetonate, cobalt (II) hexafluoroacetylacetonate, cobalt (II) picolinate, manganese (III) acetate, manganese (II) acetate, manganese (II) hexafluoroacetylacetonate trihydrate, manganese (III) acetylacetonate, manganese (II) acetylacetonate, manganese dichloride tetrahydrate, manganese dibromide, manganese (II) picolinate, manganese (III) picolinate, manganese (III) bromide acetylacetonate, vanadyl (IV) acetate (VO[OC(O)CH$_3$]$_2$), vanadyl (IV) acetylacetonate, copper (I) acetate, molybdenyl (VI) acetylacetonate (MoO$_2$[C$_5$H$_7$O$_2$]), iron (II) acetate, and hydrates, and anhydrous compounds, and mixtures thereof. In some particular embodiments metal catalysts include mixtures of cobalt (II) bromide hexahydrate with either cobalt (II) picolinate, manganese (II) bromide, manganese (II) chloride tetrahydrate, manganese (III) bromide acetylacetonate, manganese (II) acetate, manganese (III) acetate dihydrate, manganese (II) acetylacetonate, manganese (III) acetylacetonate, or manganese (II) hexafluoroacetylacetonate trihydrate; mixtures of cobalt (II) acetate with manganese (III) acetate or manganese (II) bromide; and ternary mixtures of cobalt (II) acetate with manganese (III) acetate and manganese (II) bromide; or of cobalt (II) acetate with manganese (III) acetate and cobalt(II) bromide; or of cobalt (II) acetate with manganese (III) acetate and iron (II) bromide; or of cobalt (II) acetate with manganese (III) acetate and either copper (I) bromide or copper (II) bromide. It is to be understood that reaction products of any of the above catalysts may also be present in products derived from oxidation of ortho-dialkylaromatic compounds in certain embodiments. Said reaction products may be readily identified by those skilled in the art and comprise any that may arise under the reaction conditions employed to prepare the products derived from oxidation of ortho-dialkylaromatic compounds.

When at least one metal catalyst or reaction product thereof is present, the molar ratio of the at least one metal catalyst to the ortho-dialkylaromatic oxidation product or mixture of oxidation products is in one embodiment in a range of about 1: 20–600, in another embodiment in a range of about 1:50–300, and in still another embodiment in a range of about 1:80–250. In some particular embodiments the molar ratio of the at least one metal catalyst to the ortho-dialkylaromatic oxidation product or mixture of oxidation products is about 1:200.

In various embodiments the products derived from oxidation of ortho-dialkylaromatic compounds may further comprise at least one promoter. Suitable promoters include, but are not limited to, (i) imides such as phthalimide, 4-chloro-phthalimide, 3-chloro-phthalimide, dichloro-phthalimide, N-hydroxyethylphthalimide, and N-hydroxymethylphthalimide;

(ii) N-hydroxy imides such as N-hydroxyphthalimide, 4-chloro-N-hydroxyphthalimide, 3-chloro-N-hydroxyphthalimide, dichloro-N-hydroxyphthalimide, 4-bromo-N-hydroxyphthalimide, 3-bromo-N-hydroxyphthalimide, dibromo-N-hydroxyphthalimide, N-hydroxymaleimide, and N-hydroxysuccinimide;

(iii) hydroxamic acids such as 2-carboxyethanehydroxamic acid, 2-carboxyethenehydroxamic acid, and 2-carboxyphenylhydroxamic acids of formula I:

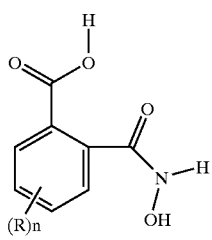

(I)

wherein each R is independently halogen, preferably chloro or bromo; or alkyl, and n is 0–4;

(iv) arylaldehydes such as substituted benzaldehydes of the formula (II):

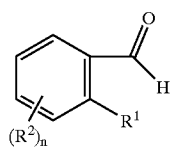

(II)

wherein $R^1$ is alkyl and each $R^2$ is independently halogen, preferably chloro or bromo; or alkyl, and n is 0–4;

(v) onium halides such as ammonium halides and phosphonium halides, preferably chlorides or bromides;

(vi) guanidinium halides, preferably chlorides or bromides; and (vii) alkali metal halides, preferably chlorides or bromides.

In various embodiments hydroxamic acids include, but are not limited to, unsubstituted 2-carboxyphenylhydroxamic acid, 4-chloro-2-carboxyphenylhydroxamic acid, 3-chloro-2-carboxyphenylhydroxamic acids, and dichloro-2-carboxyphenylhydroxamic acid. In various embodiments arylaldehydes include, but are not limited to, alkylchlorobenzaldehydes such as 3-chloro-2-methylbenzaldehyde, 4-chloro-2-methylbenzaldehyde, and dichloro-2-methylbenzaldehyde. In various embodiments onium halides include, but are not limited to, tetraalkylammonium bromides such as tetraethylammonium bromide and tetrabutylammonium bromide. In various embodiments guanidinium halides include hexaethylguanidinium chloride and hexaethylguanidinium bromide. In various embodiments an alkali metal halide is sodium bromide. In some particular embodiments of the invention promoters are N-hydroxyphthalimide and 4-chloro-N-hydroxyphthalimide.

The term "alkyl" as used in the various embodiments of the present invention is intended to designate both normal alkyl, branched alkyl, aralkyl, and cycloalkyl radicals. In various embodiments normal and branched alkyl radicals are those containing from 1 to about 30 carbon atoms, and include as illustrative non-limiting examples methyl, ethyl, n-propyl, isopropyl, n-butyl, sec-butyl, tertiary-butyl, pentyl, neopentyl, hexyl, heptyl, octyl, nonyl, decyl, undecyl and dodecyl. In various embodiments cycloalkyl radicals represented are those containing from 3 to about 12 ring carbon atoms. Some illustrative non-limiting examples of these cycloalkyl radicals include cyclobutyl, cyclopentyl, cyclohexyl, methylcyclohexyl, and cycloheptyl. In various embodiments aralkyl radicals are those containing from 7 to about 14 carbon atoms; these include, but are not limited to, benzyl, phenylbutyl, phenylpropyl, and phenylethyl. In various embodiments aryl radicals used in the various embodiments of the present invention are those containing from 6 to 12 ring carbon atoms. Some illustrative non-limiting examples of these aryl radicals include phenyl, biphenyl, and naphthyl. Halogen radicals used in some embodiments of the present invention are fluorine, chlorine and bromine.

In some embodiments the amount of promoter, when present, may have a value in one embodiment in a range between about 0.01 mole % and about 20 mole %, in another embodiment between about 0.1 mole % and about 12 mole %, and in still another embodiment between about 0.4 mole % and about 10 mole %, based on ortho-dialkylaromatic oxidation product or mixture of oxidation products.

In the context of the present invention removal of an impurity from products derived from oxidation of ortho-dialkylaromatic compounds is sometimes referred to as purification, and a resulting product may be referred to as purified. It should be understood that purification may not necessarily imply that all types of impurity are removed from an oxidation product or that all of a particular impurity is removed from an oxidation product. It should also be understood that, although products in the plural are sometimes referred to in connection with products derived from oxidation of ortho-dialkylaromatic compounds, said products may consist essentially of a single oxidation product or may comprise more than one oxidation product.

In one embodiment of the present invention products derived from oxidation of an ortho-dialkylaromatic compound are purified by a process which comprises extraction of an aqueous solution comprising dicarboxylic acid product with an organic solvent. At least one extraction is performed although in some embodiments more than one extraction may be performed. In a particular embodiment impurities removed by extraction with organic solvent comprise at least one phthalide. In the present context the term phthalide includes substituted or unsubstituted monocyclic and polycyclic phthalides, including but is not limited to, substituted or unsubstituted monocyclic or polycyclic phthalides of either formulas (III), (IV), (V) or (VI), or positional isomers thereof;

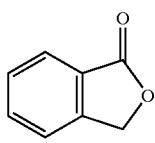

(III)

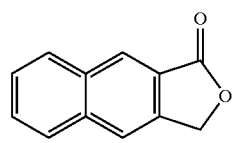

(IV)

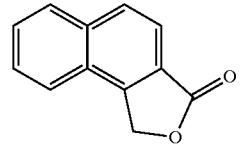

(V)

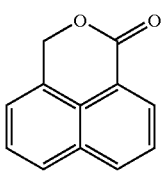 (VI)

In some particular embodiments phthalides are substituted with at least one halogen substituent. In other particular embodiments phthalides are substituted with at least one chloro substituent.

In other particular embodiments an ortho-dialkylaromatic compound comprises at least one halo-ortho-xylene and impurities removed by extraction with organic solvent comprise at least one halophthalide. In other particular embodiments a halo-ortho-xylene comprises at least one chloro-ortho-xylene and impurities removed by extraction with organic solvent comprise at least one chlorophthalide.

In one embodiment of the invention at least one extraction may be done directly on a mixture comprising volatile materials such as solvent and products derived from oxidation of an ortho-dalkylaromatic compound. Soluble impurities comprising phthalides are taken into organic solvent while the desired aromatic ortho-dicarboxylic acids are retained in the aqueous phase. In a particular embodiment soluble impurities comprising chlorophthalides are taken into organic solvent while desired chlorophthalic acids are retained in the aqueous phase. In another embodiment the mixture comprising products derived from oxidation of an ortho-dialkylaromatic compound may be evaporated to dryness under reduced pressure with heating, for example to remove volatile materials such as solvent, if present. Essentially all or at least a portion of volatile materials may be removed in this step. In one embodiment essentially all volatile materials are removed from the mixture, which means that no more liquid condensate can be collected from the mixture heated under reduced pressure. In order to ensure that any anhydrides formed during this evaporation step are reconverted to the aromatic ortho-dicarboxylic acids, the solid residue or slurry from evaporation is typically exposed to a solution comprising water at a convenient temperature, followed by extraction of aqueous phase with an organic solvent. In particular embodiments the solid residue or slurry from evaporation is typically exposed to a solution comprising water for a time and at a temperature sufficient to convert essentially all anhydride, if present, to dicarboxylic acid. The presence of anhydride in the mixture can readily be determined without undue experimentation using analytical methods known to those skilled in the art. In one particular embodiment the solid residue from evaporation may be exposed to water at a temperature of at least about 50° C., followed by extraction of the aqueous phase with organic solvent. If anhydrides are present in the mixture, it has been found that they will typically be extracted with impurities such as phthalides into organic solvent resulting in a loss in yield of oxidation products.

In various embodiments products derived from oxidation of an ortho-dialkylaromatic compound and comprising aromatic dicarboxylic acid are present in an aqueous phase in one embodiment at a level of greater than about 5 wt. %, in another embodiment at a level of greater than about 10 wt. %, in another embodiment at a level of greater than about 15 wt. %, in another embodiment at a level of greater than about 20 wt. %, in another embodiment at a level of greater than about 25 wt. %, in another embodiment at a level of greater than about 30 wt. %, and in still another embodiment at a level of greater than about 35 wt. %, based on the weight of the entire aqueous phase. In some particular embodiments products derived from oxidation of an ortho-dialkylaromatic compound and comprising aromatic dicarboxylic acid are present in an aqueous phase at a level in a range of between about 18 wt. % and about 26 wt. %, based on the weight of the entire aqueous phase.

Organic solvents which may be used in an extraction include aromatic solvents such as benzene, substituted benzenes, alkylbenzenes, toluene, xylene, halogenated benzenes, chlorobenzene, dichlorobenzene, halogenated alkylbenzenes, chlorotoluene, chloroxylene, 3-chloro-ortho-xylene, 4-chloro-ortho-xylene, alkoxybenzenes, anisole, halogenated alkoxybenzenes, and mixtures of aromatic solvents. Extraction with organic solvent may be performed at a convenient temperature between about ambient temperature and about the boiling point of water. In some embodiments extraction with organic solvent is performed at a temperature in a range of between about ambient temperature and about 80° C. In other embodiments extraction with organic solvent is performed at a temperature in a range of between about ambient temperature and about 65° C.

In one embodiment the efficacy of a solvent extraction may be measured by the distribution coefficient, K, which is the mole fraction of specified solute in the organic solvent phase compared to the mole fraction of specified solute in the aqueous phase. In some particular embodiments an organic solvent is employed such that the value of the distribution coefficient, K, for phthalide in a product mixture comprising at least one phthalic acid is greater than 1. In other particular embodiments an organic solvent is employed such that the value of the distribution coefficient, K, for chlorophthalide in a product mixture comprising at least one chlorophthalic acid is greater than 1. In various particular embodiments an organic solvent is employed such that the value of the distribution coefficient, K, for chlorophthalide is in one embodiment in a range of between about 1.1 and about 5, and in another embodiment in a range of between about 1.1 and about 4. In a particular embodiment the distribution coefficient is measured for 4-chlorophthalide with water and various organic solvents such as toluene and xylene.

Another factor for measuring the efficacy of a solvent extraction is the selectivity factor, $\beta$, which compares the ratio of two components of interest in one phase to the ratio of the same two components in the other phase. In a particular embodiment the selectivity factor is measured for 4-chlorophthalide in relation to chlorophthalic acids in both water and organic solvent.

When the products derived from oxidation of ortho-dialkylaromatic compounds comprise chlorophthalic acids, values of K are in the range of about 1.5–2.5 for toluene, xylene and o-dichlorobenzene when the original concentrations of chlorophthalic acids are about 20 wt. % and chlorophthalide concentration is about 0.6% based on the weight of the entire mixture. This means there is a preference for solubility of chlorophthalide in the organic solvent. However, the selectivity numbers for chlorophthalic acids and chlorophthalide are in the 4000–5000 range for toluene and xylene while closer to 500 for o-dichlorobenzene reflecting a low solubility of the chlorophthalic acids in toluene and xylene, and increased solubility in o-dichlorobenzene.

When levels of acetic acid ranged from 0–35 wt. % based on the weight of the water, the values for K for chlorophthalic acids and chlorophthalide at 22 wt. % solids are also in the range of about 1.7–2.6, but the selectivity numbers decrease for toluene from 4000 at 0 wt. % acetic acid to about 400 at 18 wt. % acetic acid consistent with an increased solubility in toluene due to a partitioning of the acetic acid.

In various embodiments of the invention the amount of phthalide remaining after extraction with organic solvent of products derived from oxidation of ortho-dialkylaromatic compounds may be less than about 10 wt. % of the phthalide originally present. In particular embodiments the amount of halophthalide remaining after extraction with organic solvent of products derived from oxidation of halo-ortho-dialkylaromatic compounds may be less than about 10 wt. % of the halophthalide originally present. In other particular embodiments the amount of chlorophthalide remaining after extraction with organic solvent of products derived from oxidation of chloro-ortho-xylene may be in one embodiment less than about 10 wt. % of the chlorophthalide originally present, in another embodiment less than about 5 wt. % of the chlorophthalide originally present, and in still another embodiment less than about 2 wt. % of the chlorophthalide originally present. In other particular embodiments the amount of chlorophthalide remaining after extraction with organic solvent of products derived from oxidation of chloro-ortho-xylene may be undetectable using an appropriate analytical method. In such cases essentially all chlorophthalide has been removed. Appropriate analytical methods include those known in the art and are readily determined without undue experimentation. In particular embodiments appropriate analytical methods include at least one of gas chromatography, liquid chromatography, or nuclear magnetic resonance spectroscopy.

In another embodiment of the present invention products derived from oxidation of an ortho-dialkylaromatic compound are purified by a process which comprises extraction of an organic solution comprising aromatic anhydride product with an aqueous bicarbonate solution for a time period insufficient to allow hydrolysis of anhydride to acid. At least one extraction is performed although in some embodiments more than one extraction may be performed. In a particular embodiment impurities removed by extraction with aqueous bicarbonate solution comprise a substituted or unsubstituted aromatic mono-carboxylic acid. In another particular embodiment impurities removed by extraction with aqueous bicarbonate solution comprise at least one halo-aromatic mono-carboxylic acid. In other particular embodiments an ortho-dialkylaromatic compound comprises at least one halo-ortho-xylene and impurities removed by extraction with aqueous bicarbonate solution comprise halo-benzoic acid. In other particular embodiments a halo-ortho-xylene comprises at least one chloro-ortho-xylene and impurities removed by extraction with aqueous bicarbonate solution comprise chlorobenzoic acid. In embodiments wherein at least one halo-aromatic mono-alkyl-mono-carboxylic acid is present in an oxidation reaction mixture comprising aromatic anhydride product, then this species will constitute an impurity and will also be removed by extraction with aqueous bicarbonate solution. An illustrative example of a halo-aromatic mono-alkyl-mono-carboxylic acid is chlorotoluic acid.

In various embodiments the aqueous bicarbonate solution comprises an alkali metal bicarbonate. In particular embodiments the aqueous bicarbonate solution comprises at least one of sodium bicarbonate or potassium bicarbonate.

The concentration of bicarbonate in aqueous solution may be between about 0.05 wt. % (based on the total weight of the solution) and about the concentration at which the aqueous solution is saturated with bicarbonate at the temperature of extraction. In some particular embodiments the concentration of sodium bicarbonate in aqueous solution is in a range of in one embodiment between about 0.1 wt. % and about 10 wt. %, and in another embodiment between about 1 wt. % and about 6 wt. %, based on the total weight of the solution.

The products derived from oxidation of an ortho-dialkylaromatic compound are present in an organic solvent before extraction with aqueous bicarbonate solution. Suitable organic solvents include those in which the products derived from oxidation of an ortho-dialkylaromatic compound are substantially soluble at the temperature of extraction. Suitable solvents comprise aromatic solvents such as benzene, substituted benzenes, alkylbenzenes, toluene, xylene, halogenated benzenes, chlorobenzene, dichlorobenzene, halogenated alkylbenzenes, chlorotoluene, chloroxylene, 3-chloro-ortho-xylene, 4-chloro-ortho-xylene, alkoxybenzenes, anisole, halogenated alkoxybenzenes, and mixtures of aromatic solvents.

In various embodiments products derived from oxidation of an ortho-dialkylaromatic compound and comprising aromatic anhydride are present in an organic solvent in one embodiment at a level of greater than about 5 wt. %, in another embodiment at a level of greater than about 10 wt. %, in another embodiment at a level of greater than about 15 wt. %, in another embodiment at a level of greater than about 20 wt. %, in another embodiment at a level of greater than about 25 wt. %, in another embodiment at a level of greater than about 30 wt. %, and in still another embodiment at a level of greater than about 35 wt. %, based on the weight of the entire organic phase.

In some embodiments both aromatic dicarboxylic acid and the corresponding anhydride are present in an oxidation reaction mixture. In such embodiments it is desirable to convert any aromatic dicarboxylic acid to the corresponding anhydride before extraction with aqueous bicarbonate solution. Conversion of aromatic dicarboxylic acid to the corresponding anhydride may be performed by any known dehydration method. The presence of aromatic dicarboxylic acid in the mixture can readily be determined without undue experimentation using analytical methods known to those skilled in the art.

The molar amount of bicarbonate in aqueous solution is in some embodiments such that all acidic impurities may be removed by extraction of an organic phase comprising anhydride products derived from oxidation of an ortho-dialkylaromatic compound. The level of acidic impurities can readily be determined by standard methods known to those skilled in the art without undue experimentation. In a particular embodiment the molar amount of sodium bicarbonate in aqueous solution is at least equal to the molar amount of acidic species in an organic solution of anhydride products derived from oxidation of an ortho-dialkylaromatic compound. In another embodiment the molar amount of sodium bicarbonate in aqueous solution is in excess of the molar amount of acidic species in an organic solution of anhydride products derived from oxidation of an ortho-dialkylaromatic compound. In another particular embodiment the molar amount of sodium bicarbonate in aqueous solution is at least equal to the molar amount of aromatic mono-carboxylic acid impurities in an organic solution of anhydride products derived from oxidation of an ortho-dialkylaromatic compound. In another particular embodiment the molar amount of sodium bicarbonate in aqueous solution is in excess of the molar amount of aromatic mono-carboxylic acid impurities in an organic solution of anhydride products derived from oxidation of an ortho-dialkylaromatic compound. In another particular embodiment the molar amount of sodium bicarbonate in aqueous solution is in a range of 3–10 equivalents compared to the molar amount of aromatic mono-carboxylic acid impurities in an organic solution of anhydride products derived from oxidation of an ortho-dialkylaromatic compound.

Extraction with aqueous bicarbonate solution may be performed at a convenient temperature. In some embodiments said temperature is below ambient temperature. In other embodiments said temperature is in a range of between about ambient temperature and about the boiling point of water. In some embodiments extraction with aqueous bicarbonate solution is performed at a temperature in a range of between about ambient temperature and about 80° C. In other embodiments extraction with aqueous bicarbonate solution is performed at a temperature in a range of between about ambient temperature and about 65° C. In still other embodiments extraction with aqueous bicarbonate solution is performed at a temperature in a range of between about ambient temperature and about 40° C.

The amount of time for an extraction with aqueous bicarbonate solution is such that aromatic anhydride is not significantly hydrolyzed to aromatic ortho-dicarboxylic acid. In particular embodiments the amount of time for an extraction with aqueous bicarbonate solution is such that in one embodiment less than about 10 mole % of anhydride is hydrolyzed to aromatic ortho-dicarboxylic acid, in another embodiment less than about 5 mole % of anhydride is hydrolyzed to aromatic ortho-dicarboxylic acid, in another embodiment less than about 2 mole % of anhydride is hydrolyzed to aromatic ortho-dicarboxylic acid, and in still another embodiment less than about 1 mole % of anhydride is hydrolyzed to aromatic ortho-dicarboxylic acid. In some embodiments the amount of time for an extraction with aqueous bicarbonate solution is such that aromatic ortho-dicarboxylic acid may be undetectable using an appropriate analytical method. In such cases essentially no aromatic anhydride has been hydrolyzed to aromatic ortho-dicarboxylic acid. Appropriate analytical methods include those known in the art and are readily determined without undue experimentation. In particular embodiments appropriate analytical methods include at least one of gas chromatography, liquid chromatography, or nuclear magnetic resonance spectroscopy. Those skilled in the art will realize that the amount of time for an extraction with aqueous bicarbonate solution such that little or essentially no anhydride is hydrolyzed to aromatic ortho-dicarboxylic acid may depend on the temperature of extraction, the mode of mixing the aqueous and organic phases, the relative volume of aqueous and organic phases, the total volume of aqueous and organic phases, the concentration of bicarbonate in the aqueous phase and of oxidation products in the organic phase, and the phase separation time among other factors. Under any conditions, said amount of time can be readily determined by those skilled in the art without undue experimentation. In various embodiments the amount of time for an extraction with aqueous bicarbonate solution is in one embodiment less than about 30 minutes, in another embodiment less than about 25 minutes, in another embodiment less than about 20 minutes, in another embodiment less than about 15 minutes, in another embodiment less than about 10 minutes, and in still another embodiment less than about 5 minutes.

In some embodiments wherein extraction is performed on an organic solution comprising chloro aromatic anhydride and chloro-mono-carboxylic acid impurity derived from oxidation of a chloro-ortho-dialkylaromatic compound, it has been found that an extraction time of longer than a certain time results in all chloro-mono-carboxylic acid which had been initially extracted into the aqueous phase returning to the organic phase from which it was extracted. Although the invention is in no way limited by theory of operation, it is believed that after a certain time chloro aromatic anhydride may hydrolyze to chloro aromatic dicarboxylic acid which is a stronger acid than chloro-mono-carboxylic acid and which reprotonates chloro-mono-carboxylate in the aqueous phase to regenerate the organic soluble chloro-mono-carboxylic acid with concomitant removal of a portion of chloro aromatic dicarboxylic acid to the aqueous phase. Following extraction with aqueous bicarbonate solution the organic solution may be washed with water, if so desired.

In one embodiment of the invention impurities are removed from products derived from oxidation of ortho-dialkylaromatic compounds by a method which comprises both extraction of an aqueous solution comprising aromatic dicarboxylic acid product with an organic solvent and extraction of an organic solution comprising aromatic anhydride product with an aqueous bicarbonate solution for a time period insufficient to allow hydrolysis of anhydride to acid.

The process of the present invention in its various embodiments may be performed in batch mode or semi-continuous mode or continuous mode. Any extraction method known in the art may be employed. Following removal of impurities by processes as described herein, the products derived from oxidation of ortho-dialkylaromatic compounds may be either subjected to further purification processes, and/or used in solution, and/or isolated by conventional means, such as by using isolation processes comprising one or more steps of distillation, extraction, or drying. In addition any aromatic ortho-diacid may be converted to the corresponding anhydride by dehydration, or any aromatic ortho-anhydride may be converted to the corresponding diacid by hydration, if so desired. Aromatic dicarboxylic acids and aromatic anhydrides may also be converted to other derivatives such as, but not limited to, esters, amides or imides, if so desired. In another embodiment the impurities removed from the oxidation products using a process of the present invention are recycled into a further oxidation process to increase conversion to oxidation products. For example, in one embodiment phthalides removed from the oxidation products are recycled into a further oxidation process to increase conversion to diacid and/or anhydride oxidation products.

In various embodiments when the purified product comprises halophthalic anhydrides (or halophthalic acids which may be converted to halophthalic anhydrides), they may be used in processes to make various types of aromatic polyethers, particularly aromatic polyetherimides. In one embodiment a purified product comprising 4-chlorophthalic anhydride (or a mixture thereof with 3-chlorophthalic anhydride) may be reacted with at least one diamine to prepare bis(chlorophthalimide) compounds which can serve as monomer for polyetherimide synthesis. For example, polyetherimides are conveniently prepared by the reaction of salts of dihydroxyaromatic compounds, such as a bisphenol A disodium salt, with bis(halophthalimides) as illustrated by 1,3-bis[N-(4-chlorophthalimido)]benzene, which has the structure.

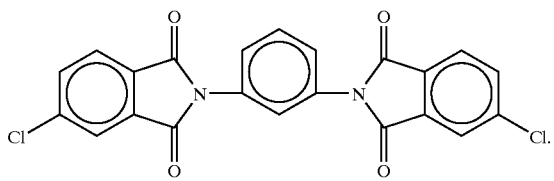

According to U.S. Pat. Nos. 5,229,482 and 5,830,974, the preparation of aromatic polyethers may be conducted in solution in relatively non,polar solvents, using a phase transfer catalyst which is substantially stable under the temperature conditions employed. Solvents disclosed in U.S. Pat. No. 5,229,482 include o-dichlorobenzene, dichlorotoluene, 1,2,4-trichlorobenzene and diphenyl sulfone. In U.S. Pat. No. 5,830,974, monoalkoxybenzenes such as anisole, diphenylether, or phenetole are employed. Solvents of the same types may be used for the preparation of bis(halophthalimide) intermediates, particularly bis (chlorophthalimide) intermediates, for polyetherimides.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLE 1

A 35 wt. % solution of crude chlorophthalic acid in water was prepared by adding appropriate amounts of 4- and 3-chlorophthalic anhydride (70/30 isomer ratio) along with a mixture of about 3 wt. % (based on crude chlorophthalic anhydride) of synthetic 4- and 7-chlorophthalide (produced by reduction of 3-chlorophthalic anhydride). This mixture was stirred at approximately 60° C. for 2 hours after which all of the chlorophthalic anhydride had hydrolyzed to chlorophthalic acid as shown by gas chromatographic (GC) analysis which showed no anhydride in the extracted organic phase. A number of vials were prepared each containing 5 milliliters (ml.) of an aqueous phase comprising a certain concentration of crude chlorophthalic acid (5 wt. % to 35 wt. %, based on the weight of the entire aqueous phase and, optionally, acetic acid (0 wt. % to 36 wt. %, based on the weight of the entire aqueous phase). Each vial was then treated with 5 ml. of either toluene, o-dichlorobenzene (ODCB), or ortho-xylene. The vials were then shaken vigorously in a mechanical shaker for 50 minutes at a specified temperature (22° C., 42° C., or 60° C.). The phases were allowed to separate over several hours (actual phase separation occurred much quicker than this) and then each phase was sampled using a pipette. No stable emulsions were observed under the conditions which were examined. The organic phase was analyzed directly by GC (using biphenyl internal standard, following silylation of the product mixture), while for the aqueous phase, water was evaporated and solid residue was redissolved in organic solvent before GC analysis. The analytical data were used to calculate an equilibrium constant, K, which represented the ratio of chlorophthalides mass fraction in the organic phase to that in the aqueous phase. The analytical data were also used to calculate a selectivity constant, beta, which represented the quotient of [(wt. fraction of chlorophthalides in xylene)/(wt fraction of chlorophthalic acids in xylene)] divided by the quotient of [(wt fraction of chlorophthalides in water)/(wt fraction of chlorophthalic acids in water)]. The data in Table 1 show results of extractions performed at 22° C. with no acetic acid present.

TABLE 1

| Wt. % of chlorophthalic acid in aqueous phase | K values | | | beta values | | |
|---|---|---|---|---|---|---|
| | toluene | xylene | ODCB | toluene | xylene | ODCB |
| 5.5 | — | — | 1.1 | — | — | 400 |
| 6 | 1.8 | — | — | 800 | — | — |
| 12 | 2.6 | 2.5 | 1.8 | 2500 | 3500 | 800 |
| 23 | 2.5 | 1.8 | 2.2 | 3900 | 4700 | 300 |
| 35 | 1.7 | 1.3 | 1.4 | 3400 | 4200 | 260 |

The data show that there is a dependence of K on initial chlorophthalic acid concentration, and that xylene and toluene have a much higher selectivity for chlorophthalides over 3 and 4-chlorophthalic acids than does ODCB under these conditions.

EXAMPLES 2

The Procedure of Example 1 was repeated except that extractions were performed at 22 wt. % initial chlorophthalic acid concentration at 22° C. in the presence of different levels of acetic acid. The data are shown in Table 2.

TABLE 2

| Wt. % of acetic acid in initial aqueous phase | K values | | beta values | |
|---|---|---|---|---|
| | toluene | ODCB | toluene | ODCB |
| 9 | — | 2.3 | — | 200 |
| 17 | 2.5 | 2.2 | 400 | 200 |
| 26 | 2.2 | 1.9 | 150 | 100 |
| 35 | — | 1.7 | — | 100 |
| 36 | 1.9 | — | 100 | — |

The data show that the addition of increasing amounts of acetic acid decreases both K and beta values when toluene or ODCB are used as extractants under these conditions. Similar trends were observed when xylene was used as the extraction solvent at both 30° C. and 60° C.

EXAMPLES 3

The procedure of Example 1 was repeated except that extractions were performed at different wt. % initial chlorophthalic acid concentration at 60° C. with no acetic acid present. The data are shown in Table 3.

TABLE 3

| Wt. % of chlorophthalic acid in aqueous phase | K values | | beta values | |
|---|---|---|---|---|
| | toluene | ODCB | toluene | ODCB |
| 22 | 3.5 | 2.8 | 1800 | 800 |
| 35 | 2.0 | 1.7 | 1400 | 800 |

The data show that under these conditions K values for extraction increase with increasing temperature in the absence of acetic acid when toluene or ODCB are used as extractants, while selectivity increases or decreases depending upon extraction solvent. When either xylene or 4-chloro-o-xylene was used as extraction solvent at 30° C., both the K values and the selectivity values were similar and decreased with increasing level of chlorophthalic acid in the aqueous phase. Similar trends were observed when xylene was used as extraction solvent at 60° C., and in addition the K values and selectivity values were lower than those obtained at 30° C.

EXAMPLE 4

The procedure of Example 1 was repeated except that extractions were performed at 22 wt. % initial chlorophthalic acid concentration at 60° C. in the presence of different levels of acetic acid. The data are shown in Table 4.

TABLE 4

| Wt. % of acetic acid in initial | K values | | beta values | |
|---|---|---|---|---|
| aqueous phase | toluene | ODCB | toluene | ODCB |
| 10 | 3.3 | 3.1 | 900 | 600 |
| 19 | 2.9 | 2.5 | 300 | 300 |
| 29 | 2.4 | 2.3 | 150 | 150 |
| 37 | — | 1.7 | — | 100 |
| 38 | 1.6 | — | 50 | — |

The data show that K values for extraction increase with increasing temperature in the presence of acetic acid when toluene or ODCB are used as extractants under these conditions, while selectivity increases or decreases depending upon extraction solvent.

EXAMPLE 5

Other experiments were carried out on actual oxidation mixtures from reactions of 3- and 4-chloroxylene with oxygen in acetic acid in the presence of a catalyst. In some cases the catalyst components were removed by precipitation, for example with oxalic acid, but the low levels of metals present in those samples still containing catalyst components did not affect the solubility characteristics of the organic species. At least a portion of oxidation reaction mixture was distilled in vacuo to remove acetic acid, leaving a solid residue which was dissolved in water. The extraction of a 30 wt. % aqueous solution of 3- and 4-chloroxylene oxidation mixture was carried out with xylene. Six extractions were made starting with 130 kilograms (kg.) of solution extracting the aqueous phase with 155 kg. of xylene. At the beginning the temperature was approximately 35° C., and later was raised to 40° C. to present the crystallization of chlorophthalic acid. The results of extraction are shown Table 5. Unless noted, the values in the table represent relative percentages in the composition of the designated components (total percentage equals 100%).

TABLE 5

| Extraction number | Watery phase amount obtained (kg.) | 3-chloro-PA | 4-chloro-PA | 5-chloro-phthalide | 4-chloro-phthalide | Low boiling point fraction | High boiling point fraction |
|---|---|---|---|---|---|---|---|
| 0 | 130 | 29.2 | 65.4 | 1.02 | 2.97 | 0.63 | 0.82 |
| 1 | 140.5 | 30.5 | 67.5 | 0.31 | 0.67 | 0.8 | 0.21 |
| 2 | 132.4 | 31 | 68 | 0.11 | 0.19 | 0.61 | 0.12 |
| 3 | 132.2 | 30.9 | 68.5 | 0.03 | 0.04 | 0.41 | 0.11 |
| 4 | 129.2 | 30.8 | 68.5 | 0.02 | <0.01 | 0.62 | 0.09 |
| 5 | 127.1 | 30.9 | 68.1 | <0.01 | <0.01 | 0.85 | 0.09 |
| 6 | 121 | 30.8 | 68.1 | <0.01 | <0.01 | 1.07 | 0.06 |

The effective purity of chlorophthalic anhydrides increased from 94.6% to 98.9% as a result of the extractions.

EXAMPLE 6

A 4.98 g. sample of an oxidation solution in acetic acid from the oxidation of 3- and 4-chloroxylene was combined with 12 ml. of ODCB and 11 ml. of water and mixed. The ODCB phase was analyzed directly without removal of solvent and the water phase was analyzed after stripping solvent and redissolving in tetrahydrofuran. The water phase contained about 1.5 g. of solids The analytical results are shown in Table 6.

TABLE 6

| GC analysis after silylation | 4-Cl phthalide | 4-Cl phthalic acid | 3-Cl phthalic acid |
|---|---|---|---|
| ODCB phase | 11.1% | 70.8% | 18.1% |
| Water phase | 0.2% | 70.8% | 29.0% |

EXAMPLE 7

A 45.85 g sample of an oxidation mixture in acetic acid from the oxidation of 3- and 4-chloroxylene in the presence of a catalyst composition comprising cobalt and manganese was treated with 0.143 g. of oxalic acid dihydrate and brought to reflux for 30 minutes (this process removed about 90% of the cobalt and >50% of the manganese by precipitation as the oxalate salts). The solution was then passed through a glass frit under vacuum. The remainder of the solvent was removed by evaporation (down to 16.2 g.) and distillation (down to 14.0 g. residue). The remaining light yellow solid was combined with 60 ml. of water and 40 ml. of toluene, and mixed. There was some emulsion layer which was treated in a second wash with an additional 15 ml. each of water and toluene. The solvent was removed by evaporation of each fraction to leave 10.6 g. in the water fraction and 2.7 g. in the toluene fraction. The fractions were analyzed by GC. The analytical results are shown in Table 7.

TABLE 7

| GC analysis | 4-ClPA* | 4-Cl phthalide | 3-ClPA* | 4-Cl phthalic acid | 3-Cl phthalic acid |
|---|---|---|---|---|---|
| Water phase | — | 0.1% | — | 72.6% | 27.3% |
| Toluene phase | 48.0% | 2.0% | 29.1% | 14.1% | 6.8% |
| Water phase from 2nd extraction | — | 0.1% | — | 64.0% | 36.0% |

*ClPA is chlorophthalic anhydride

The solid from the toluene phase was then immersed in 50 ml. of water overnight at 50° C. It was then extracted with toluene to generate 2.4 g. of almost white solid from the water phase and 0.2 g. from the toluene phase. Data from analyses of the water phase from the second extraction are shown in the table. The net result was about 13 g. of chlorophthalic acids and 0.2 g. of the impurity-rich phase.

EXAMPLE 8

Individual samples of chlorophthalic anhydride (ClPA) in ODCB (20% solids) containing about 0.8% (area ratio from HPLC analysis) of chlorobenzoic acid (ClBA) were extracted at room temperature with 10 molar equivalents of sodium bicarbonate as a 5% aqueous solution. As the data in Table 8 indicate (samples 1–6 at 1.5–15 minutes contact time), complete extraction of ClBA was obtained at contact times of less than 20 minutes. At a contact time of 20 minutes (sample 6) traces of ClBA were detected in the organic layer. At a contact time of 30 minutes (sample 7), the organic layer showed the presence of ClBA at a level equivalent to that present in the starting impure material.

TABLE 8

| Sample | Contact Time (min.) | ClBA in organic phase by HPLC |
|---|---|---|
| Impure ClPA | 0 | Present at ~0.8% |
| 1 | 1.5 | ND* |
| 2 | 3 | ND |
| 3 | 5 | ND |
| 4 | 10 | ND |
| 5 | 15 | ND |
| 6 | 20 | Traces of ClBA regenerated |
| 7 | 30 | Present at ~0.8% |

*ND Not detected

EXAMPLE 9

An extraction procedure similar to that of Example 8 was performed on a 25 kg. sample of an oxidation reaction mixture comprising 4-chlorophthalic anhydride and chlorobenzoic acid in 100 kg. ODCB. The bicarbonate solution comprised 700 grams sodium bicarbonate in 25 kg. deionized water. The phases were mixed for 3 minutes, allowed to separate, and the organic layer removed. The organic layer was then washed with 25 kg. deionized water for 1.5 minutes. The phases were allowed to separate and the organic layer removed. No chlorobenzoic acid could be detected in the organic layer. The organic layer was diluted with 20 kg. ODCB and dried by azeotropic distillation with removal of 20 kg. condensate. The purified product comprising 4-chlorophthalic anhydride was used to prepare a polyetherimide.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All Patents cited herein are incorporated herein by reference.

What is claimed is:

1. A method for removing impurities from products derived from oxidation of an ortho-dialkylaromatic compound which comprises the step of extracting an organic solution comprising aromatic anhydride product with an aqueous bicarbonate solution for a time period insufficient to allow hydrolysis of anhydride to acid.

2. The method of claim 1 wherein impurities comprise at least one of a substituted or unsubstituted aromatic mono-carboxylic acid.

3. The method of claim 1 wherein the products comprise at least one of a halo-aromatic dicarboxylic acid or the corresponding halo-aromatic anhydride.

4. The method of claim 3 wherein the products comprise at least one of a chloro-aromatic dicarboxylic acid or the corresponding chloro-aromatic anhydride.

5. The method of claim 1 wherein the products comprise at least one of a substituted or unsubstituted phthalic acid, or substituted or unsubstituted phthalic anhydride.

6. The method of claim 5 wherein the products comprise at least one of a halophthalic acid or halophthalic anhydride.

7. The method of claim 6 wherein the products comprise at least one of a chlorophthalic acid or chlorophthalic anhydride.

8. The method of claim 1 wherein the ortho-dialkylaromatic compound comprises at least one halo-ortho-dialkylaromatic compound.

9. The method of claim 8 wherein the halo-ortho-dialkylaromatic compound comprises at least one chloro-ortho-dialkylaromatic compound.

10. The method of claim 9 wherein the halo-ortho-dialkylaromatic compound comprises at least one of 3-chloro-ortho-xylene or 4-chloro-ortho-xylene.

11. The method of claim 9 wherein the halo-ortho-dialkylaromatic compound comprises a mixture of 3-chloro-ortho-xylene and 4-chloro-ortho-xylene.

12. The method of claim 8 wherein impurities comprise at least one halo-aromatic mono-carboxylic acid.

13. The method of claim 12 wherein impurities comprise at least one chloro-aromatic mono-carboxylic acid.

14. The method of claim 9 wherein the products comprise at least one of 3-chlorophthalic acid, 3-chlorophthalic anhydride, 4-chlorophthalic acid, or 4-chlorophthalic anhydride.

15. The method of claim 1 which further comprises the step of extracting an aqueous solution comprising aromatic dicarboxylic acid product with an organic solvent.

16. The method of claim 15 wherein the products comprise at least one of a halo-aromatic dicarboxylic acid or the corresponding halo-aromatic anhydride.

17. The method of claim 16 wherein the products comprise at least one of a chloro-aromatic dicarboxylic acid or the corresponding chloro-aromatic anhydride.

18. The method of claim 15 wherein the products comprise at least one of a substituted or unsubstituted phthalic acid, or substituted or unsubstituted phthalic anhydride.

19. The method of claim 18 wherein the products comprise at least one of a halophthalic acid or halophthalic anhydride.

20. The method of claim 19 wherein the products comprise at least one of a chlorophthalic acid or chlorophthalic anhydride.

21. The method of claim 15 wherein the ortho-dialkylaromatic compound comprises at least one halo-ortho-dialkylaromatic compound.

22. The method of claim 21 wherein the halo-ortho-dialkylaromatic compound comprises at least one chloro-ortho-dialkylaromatic compound.

23. The method of claim 22 wherein the halo-ortho-dialkylaromatic compound comprises at least one of 3-chloro-ortho-xylene or 4-chloro-ortho-xylene.

24. The method of claim 22 wherein the halo-ortho-dialkylaromatic compound comprises a mixture of 3-chloro-ortho-xylene and 4-chloro-ortho-xylene.

25. The method of claim 15 wherein impurities comprise at least one halophthalide.

26. The method of claim 25 wherein impurities comprise at least one chlorophthalide.

27. The method of claim 22 wherein the products comprise at least one of 3-chlorophthalic acid, 3-chlorophthalic anhydride, 4-chlorophthalic acid, or 4-chlorophthalic anhydride.

28. The method of claim 26 wherein the distribution coefficient of chlorophthalide between organic solvent and water is greater than 1.

29. The method of claim 28 wherein the distribution coefficient of chlorophthalide between organic solvent and water is in a range of between about 1.1 and about 5.

30. The method of claim 29 wherein the distribution coefficient of chlorophthalide between organic solvent and water is in a range of between about 1.1 and about 4.

31. The method of claim 15 wherein the organic solvent is at least one member selected from the group consisting of benzene, substituted benzenes, alkylbenzenes, toluene, xylene, halogenated benzenes, chlorobenzene, dichlorobenzene, halogenated alkylbenzenes, chlorotoluene, chloroxylene, 3-chloro-ortho-xylene, 4-chloro-ortho-xylene, alkoxybenzenes, anisole, halogenated alkoxybenzenes, and mixtures thereof.

32. The method of claim 31 wherein solvent is at least one member selected from the group consisting of toluene, xylene, chlorobenzene, dichlorobenzene, chlorotoluene, chloroxylene, 3-chloro-ortho-xylene, 4-chloro-ortho-xylene, and mixtures thereof.

33. The method of claim 15 wherein at least one extraction with organic solvent is performed at a temperature in a range of between about ambient temperature and about 80° C.

34. The method of claim 33 wherein at least one extraction with organic solvent is performed at a temperature in a range of between about ambient temperature and about 65° C.

35. The method of claim 26 wherein the level of chlorophthalide remaining following extraction with organic solvent is less than about 10 wt. % of the chlorophthalide originally present.

36. The method of claim 35 wherein essentially all chlorophthalide is removed by extraction with organic solvent.

37. The method of claim 16 wherein any halo-aromatic anhydride present is hydrolyzed to halo-aromatic acid before extraction with organic solvent.

38. The method of claim 37 wherein halo-aromatic anhydride comprises chloro-aromatic anhydride.

39. The method of claim 38 wherein chloro-aromatic anhydride comprises at least one of 3-chlorophthalic anhydride or 4-chlorophthalic anhydride.

40. The method of claim 13 wherein impurities comprise at least one chlorobenzoic acid.

41. The method of claim 1 wherein the organic solution comprises at least one of an aromatic solvent, benzene, a substituted benzene, an alkylbenzene, toluene, xylene, a halogenated benzene, chlorobenzene, dichlorobenzene, a halogenated alkylbenzene, chlorotoluene, chloroxylene, 3-chloro-ortho-xylene, 4-chloro-ortho-xylene, an alkoxybenzene, anisole, a halogenated alkoxybenzene, and mixtures thereof.

42. The method of claim 1 wherein the bicarbonate solution comprises sodium bicarbonate.

43. The method of claim 42 wherein the molar amount of sodium bicarbonate is at least equal to the molar amount of acidic species in the organic solution.

44. The method of claim 43 wherein the molar amount of sodium bicarbonate is at least equal to the molar amount of halo-aromatic mono-carboxylic acid impurity.

45. The method of claim 44 wherein the molar amount of sodium bicarbonate is in a range of 3–10 equivalents compared to the molar amount of halo-aromatic mono-carboxylic acid impurity.

46. The method of claim 1 wherein time period is less than 30 minutes.

47. The method of claim 46 wherein time period is less than 20 minutes.

48. The method of claim 1 wherein essentially all halo-aromatic mono-carboxylic acid is removed by extraction with an aqueous bicarbonate solution.

49. A method for removing impurities comprising at least one chlorophthalide and at least one chlorobenzoic acid from products derived from oxidation of at least one of 3-chloro-ortho-xylene or 4-chloro-ortho-xylene which comprises the steps of (a) extracting an aqueous solution comprising chlorophthalic acid with an organic solvent selected from the group consisting of toluene, xylene, chlorobenzene, dichlorobenzene, chlorotoluene, chloroxylene, 3-chloro-ortho-xylene, 4-chloro-ortho-xylene, and mixtures thereof, wherein essentially all chlorophthalide is removed from the aqueous phase, and (b) extracting an organic solution comprising at least one aromatic solvent and chlorophthalic anhydride with an aqueous sodium bicarbonate solution in a molar amount in a range of 3–10 equivalents compared to the molar amount of chlorobenzoic acid for a time period insufficient to allow hydrolysis of anhydride to acid, wherein essentially all chlorobenzoic acid is removed from the organic phase.

50. The method of claim 49 wherein the products comprise at least one of 3-chlorophthalic acid, 3-chlorophthalic anhydride, 4-chlorophthalic acid, or 4-chlorophthalic anhydride.

51. The method of claim 49 wherein any chlorophthalic anhydride present is hydrolyzed to chlorophthalic acid before extraction with organic solvent.

52. A method for removing impurities comprising at least one chlorobenzoic acid from products derived from oxidation of at least one of 3-chloro-ortho-xylene or 4-chloro-ortho-xylene which comprises the step of extracting an organic solution comprising at least one aromatic solvent and chlorophthalic anhydride with an aqueous sodium bicarbonate solution in a molar amount in a range of 3–10 equivalents compared to the molar amount of chlorobenzoic acid for a time period insufficient to allow hydrolysis of anhydride to acid, wherein essentially all chlorobenzoic acid is removed from the organic phase.

53. The method of claim 52 wherein time period is less than 20 minutes.

* * * * *